United States Patent
Siegel et al.

(10) Patent No.: US 8,663,782 B1
(45) Date of Patent: Mar. 4, 2014

(54) FLUID HANDLING FLOORMAT AND METHOD

(76) Inventors: David Siegel, Warren, NJ (US); Richard S. Siegel, Warren, NJ (US)

( * ) Notice: Subject to any disclaimer, the term of this patent is extended or adjusted under 35 U.S.C. 154(b) by 212 days.

(21) Appl. No.: 12/869,305

(22) Filed: Aug. 26, 2010

Related U.S. Application Data

(63) Continuation-in-part of application No. 11/935,117, filed on Nov. 5, 2007, now Pat. No. 7,785,692, which is a continuation-in-part of application No. 11/210,808, filed on Aug. 25, 2005, now Pat. No. 7,291,376, which is a continuation-in-part of application No. 10/911,935, filed on Aug. 4, 2004, now abandoned.

(60) Provisional application No. 61/287,255, filed on Dec. 17, 2009.

(51) Int. Cl.
*B32B 3/30* (2006.01)

(52) U.S. Cl.
USPC .......................................... 428/167; 428/156

(58) Field of Classification Search
USPC .......... 428/156, 158, 159, 160, 167; 137/312, 137/602; 141/86
See application file for complete search history.

(56) References Cited

U.S. PATENT DOCUMENTS

| | | | |
|---|---|---|---|
| 2,005,659 A | 6/1935 | Matteson | |
| 4,765,670 A | 8/1988 | Jackson | |
| 4,811,937 A | 3/1989 | Rothman | |
| 5,028,468 A | 7/1991 | Taylor | |
| 5,080,956 A | 1/1992 | Smith | |
| 6,102,073 A | 8/2000 | Williams | |
| 6,245,697 B1 | 6/2001 | Conrad et al. | |
| 6,568,419 B1 | 5/2003 | Robinson et al. | |
| 6,599,615 B2 * | 7/2003 | Burke et al. | 428/192 |
| 6,719,348 B1 | 4/2004 | Song | |
| 6,726,190 B2 | 4/2004 | Malpass et al. | |
| 7,291,376 B1 | 11/2007 | Siegel et al. | |
| 2002/0092563 A1 | 7/2002 | Robinson | |
| 2003/0068463 A1 | 4/2003 | Polley | |
| 2003/0232175 A1 | 12/2003 | Zahler | |
| 2004/0091674 A1 | 5/2004 | Altshuler | |
| 2006/0070654 A1 * | 4/2006 | VanBasten | 137/15.01 |
| 2008/0178957 A1 * | 7/2008 | Thomas et al. | 138/121 |

FOREIGN PATENT DOCUMENTS

JP   2005254838 A   *   9/2005

OTHER PUBLICATIONS

Partial machine translation of JP 2005254838 A; retrieved Feb. 25, 2013.*

* cited by examiner

*Primary Examiner* — Alexander Thomas

(57) ABSTRACT

A floormat for handling fluids is formed, at least in part, of compressible and resilient material. The topside of the floormat has a spaced plurality of channels feeding one or more gutters. The topside also has a central region and a border region. The central region occupies most of the topside and is substantially flat throughout except for the channels. One or more gutters in the floormat communicate with the distal ends of the channels. One or more discrete outlet gutters in the floormat allow drainage off the floormat. After placing the floormat where a user is expected to stand during the procedure, fluids that fall onto the floormat will flow from the channels to the one or more gutters for removal from one or more discrete locations on the one or more gutters.

21 Claims, 7 Drawing Sheets

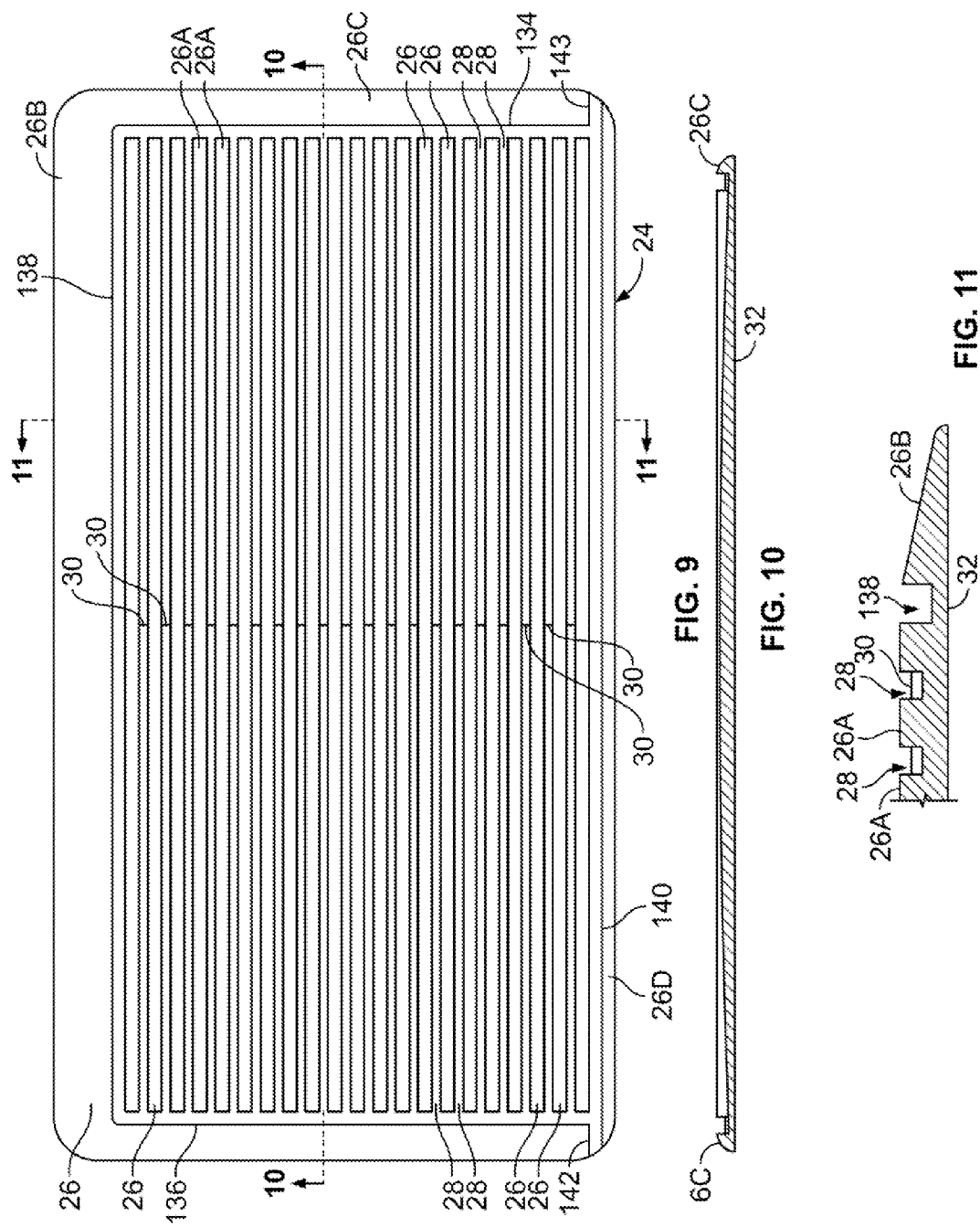

FLUID HANDLING FLOORMAT AND METHOD

CROSS REFERENCES TO RELATED APPLICATIONS

This application claims the benefit of U.S. Provisional Patent Application Ser. No. 61/287,255, filed 17 Dec. 2009, the contents of which are hereby incorporated by reference herein, and is a continuation-in-part application of U.S. patent application Ser. No. 11/935,117, filed 5 Nov. 2007 (issuing 31 Aug. 2010 as U.S. Pat. No. 7,785,692), which is in turn a continuation-in-part application of U.S. patent application Ser. No. 11/210,808, filed 25 Aug. 2005, now U.S. Pat. No. 7,291,376 which is in turn a continuation-in-part of U.S. patent application Ser. No. 10/911,935, filed 4 Aug. 2004, abandoned the contents of all being hereby incorporated by reference herein.

BACKGROUND OF THE INVENTION

1. Field of the Invention

The present invention relates to floormats and methods for handling with a floormat fluids released during surgery or released in other environments.

2. Description of Related Art

During surgery various fluids are released, which often fall onto the floor of an operating room. Not only can blood and other body fluids spill onto the floor, some procedures irrigate a surgical site with copious amounts of saline solution, which is then allowed to spill onto the floor.

It is highly desirable to quickly get these fluids away from the surgeon's feet to reduce the risk of slipping. Also, fluids released during surgery can spread infections and this risk is greatly enhanced the longer the surgeon stands or walks in these fluids. In the past surgical assistants have used existing surgical suction devices to vacuum these fluids. However, this method is not only inefficient but produces much distracting noise. Other known methods include placing towels or blankets on the fluid puddles, but this is time-consuming and requires the surgeon to step away and then stand on soaking material, which is both uncomfortable and increases the risk of tripping, as well as infection.

In addition, musculoskeletal disorders (MSDs) resulting from prolonged standing in the work place present not only a challenge to our health system in economic terms (workers compensation claims), but also place a significant burden upon the productivity, safety and health of the individual worker in the health-care environment. MSDs are injuries and illnesses that affect muscles, nerves, tendons, ligaments, cartilage and joints, spinal discs, blood vessels and bones. MSDs are not usually caused by acute trauma, but occur slowly over time due to repeated trauma to the soft tissues. Work-Related Musculoskeletal Disorders (WMSDs) are MSDs that are caused or made worse by work methods and environment. WMSDs can occur when the physical capabilities of the worker do not match the physical requirements of the job. The discomfort due to a WMSD often improves following medical treatment. Changing the work environment in order to alleviate stresses which led to the symptoms will help as well.

There have been many independent journal articles & studies, most focusing on the benefits of anti-fatigue matting (ergonomics) utilized in the work place. For example, OSHA (Occupational Safety and Health Administration) has identified static posture, contact stress and awkward postures as some of the potential workplace risk factors that cause MSDs. In the repealed "OSHA-Ergonomic Program Final rule", prolonged and static standing was identified as a risk factor and anti-fatigue matting was a control method for that risk factor.

Various other environments exist where a person may be standing during a procedure and where fluid may be spilled in the vicinity of where the person stands. For example, boaters may stand on a deck that is periodically sprayed or splashed by seawater. In some cases the boater may need to operate, repair or clean equipment and seawater may drain from the equipment during the procedure.

Also fishermen and hunters may need to clean, dress and prepare their catch or kill. In such cases fluids may run onto the ground or floor due to the release of body fluids or water used to clean the work site. Butchers will experience a similar situation when cutting and dressing meat at a butcher shop.

In addition, many technicians and hobbyists in the automotive field, gun repair/maintenance field, or other mechanical repair fields may spill fluids used to clean parts or may spill fluids used by the machinery (hydraulic fluid, coolant, brake fluid, transmission fluid, refrigerant, etc.)

Ordinary consumers may also deal with spills in the vicinity of where the person stands. Spilled fluids are often encountered when preparing foods or using the sink in a kitchen. In addition, various cleaning or repair tasks conducted throughout the house, yard or garden may involve fluid spills as well.

In U.S. Pat. No. 4,765,670 an auto mat has a number of grooves that all slope in the same direction to fill a sump formed along one edge of the mat. The reference recognizes that this sump can overflow and therefore suggests connecting the sump to a drainage tank.

In U.S. Pat. No. 6,719,348 flooring 10 is installed over a number of storage compartments 42 in the back of a motor vehicle. The top of the flooring has a number of grooves 16 arranged in a herringbone pattern and feeding two central channels 14. Fluids falling on the flooring 10 flow through grooves 16 and channels 14 into a sump 40 built into the rear of the vehicle.

In U.S. Patent Application 2002/0092563 a crowned, non-absorbent splash pad 42 is placed on a base with raised center 26 and radial drainage channels 28, which feed into lower peripheral channel 30. Fluid-removing suction tubing 50 is connected to the lower channel 30. The base is not meant to support the weight of a person.

In U.S. Patent Application 2003/0068463 a disposable, surgical floormat can be affixed to a surface using adhesive material 28 attached to a carrier sheet 26 and protected with removable liner sheet 29. Cover 60 provides a non-slip, water-resistant surface, while layers 30, 40, 50 gradually decrease in overall length and width, creating a "pyramid" effect.

In FIG. 6 of U.S. Patent Application 2004/0091674 a corrugated anti-fatigue mat has drainage holes 240.

In U.S. Pat. No. 4,811,937, operating room personal stand on a floor through which fluids pass to a slightly inclined fluid receiving surface. Fluids are directed into a trough, and evacuated through a drain which is connected to a suction device.

In U.S. Pat. No. 6,102,073 a porous, flexible mat 34 rests atop a grid 32. The grid 32 is supported by a base 12 with studs 30, which defines a floor 20 formed of three sloped segments 22, 24, and 26 along which fluids will flow. Fluids directed onto the mat will flow onto the floor 20, where they will be withdrawn through fluid outlet 28 by a suitable suction device.

In U.S. Pat. No. 6,568,419, a broad, shallow vessel 28 is used to collect fluids that pass through a foot pad 24 made of a sturdy, non-woven mat 54 that operating room personnel stand on. Fluids are removed from the vessel 28 by a drainage system 26 and stored in a collection tank 80.

In U.S. Patent Application 2003/0232175 a floor mat 100 has four folding panels 110, 120, 130, 135 with fluid-capturing recesses 290 and beveled edges 295.

In U.S. Pat. No. 6,726,190, suction cups 26 on the bottom surface 14 of a mat 20 restrict movement on the floor, and fluids can pass into holes 30 in the mat.

In U.S. Pat. No. 5,080,956 a non-porous sheet 30 made of bubble-pack material channels liquids 34 onto absorbent sheet 20.

In U.S. Pat. No. 5,028,468 a thin plastic layer 16 is inserted into an envelope 12 with an absorbent surface 14 to provide an anti-fatigue surface for surgical personnel and a means of floor protection from fluids. The thin plastic layer 16 can be removed and re-used, while the envelope 12 is discarded after each use.

In U.S. Pat. No. 6,245,697, protective, flexible mats are used for absorbing liquids, and may contain non skid material.

SUMMARY OF THE INVENTION

In accordance with the illustrative embodiments demonstrating features and advantages of the present invention, there is provided a method for handling fluids released during a procedure with a floormat having a plurality of sloped channels feeding one or more gutters. the method includes the step of placing the floormat where a user is expected to stand during the procedure. Another step is allowing fluids that fall onto the floormat to flow from the channels to the one or more gutters. The method includes the step of removing fluids from one or more discrete locations on the one or more gutters.

In accordance with another aspect of the invention, a method is provided for handling fluids released during a procedure with a floormat that has a central region with a plurality of sloped channels feeding one or more gutters. the method includes the step of placing the floormat where a user is expected to stand during the procedure. Another step is allowing fluids that fall onto the floormat to drain into the one or more gutters. The method includes the step of removing fluids from one or more discrete locations on the one or more gutters.

In accordance with yet another aspect of the invention, a floormat is arranged to handle fluids. The floormat has a topside and an underside and is formed, at least in part, of compressible and resilient material. The topside has a spaced plurality of channels feeding one or more gutters. The topside has a central region and a border region. The central region occupies most of the topside and is substantially flat throughout except for the channels. The floormat has one or more gutters that are in communication with the distal ends of the channels. The floormat also has one or more discrete outlet gutters allowing drainage off the floormat.

By employing equipment and methods of the foregoing type, fluids released during surgery or other procedures can be handled in a highly effective and efficient manner. In one embodiment a rectangular mat with rounded corners is made of an elastomeric, material for reducing fatigue and increasing comfort.

In one embodiment the surgical mat has a relatively flat topside, except for a number of longitudinal channels. The floors of these channels are sloped away from a central peak so that fluids released during a procedure flow into the channels and away from the center of the mat. For this embodiment, the mat has rounded corners and is formed of a compressible and resilient material to reduce a surgeon's fatigue.

In another embodiment, the mat has a crowned central section, which is integral with a tapered apron that encircles the central section. The apron is formed with a number of shallow channels that run from the outside border of the central section to the edge of the apron.

In both embodiments the fluids eventually drain into a gutter that runs along the periphery of the mat. The gutter can have one or more outlet gutter is so that the fluid can train to a single location away from the mat. In some embodiments, the gutter can be fitted with drainage pipes that lead to the outlet gutter. In a disclosed embodiment these drainage pipes will have apertures that are aligned with drainage channels and the pipes can be covered with a material that acts as a filter and noise suppressor. A suction hose can be attached to the drainage pipes to draw a away the draining fluid.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein:

FIG. 9 is a plan view of a floormat that is an alternate to those described above; and FIG. 10 is a sectional view taken long line 10-10 of FIG. 9;

FIG. 11 is a cross-sectional view taken long line 11-11 of FIG. 9 of a fragment of the floormat;

DETAILED DESCRIPTION OF THE PREFERRED EMBODIMENTS

Figure 1:
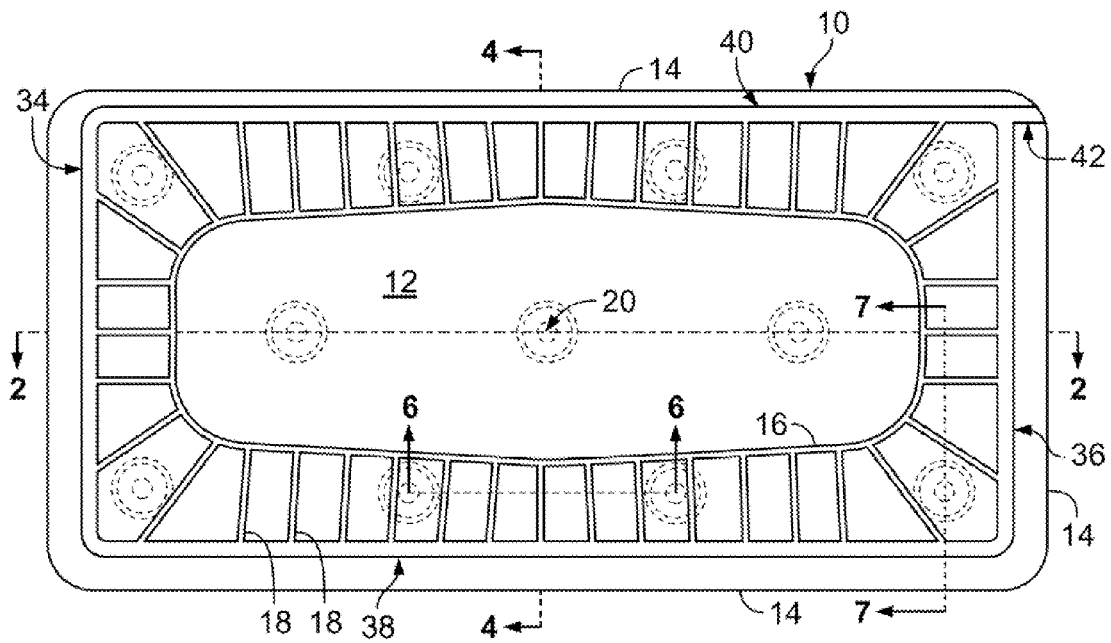
FIG. 1 is a plan view of a floormat in accordance with the present invention.
Figure 2:
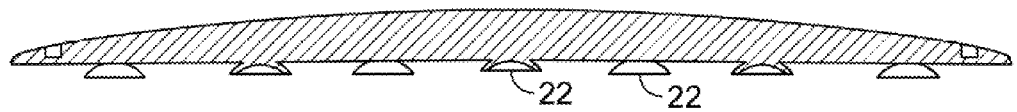
FIG. 2 is a cross-sectional view taken a long line 2-2 of FIG. 1.
Figure 3:
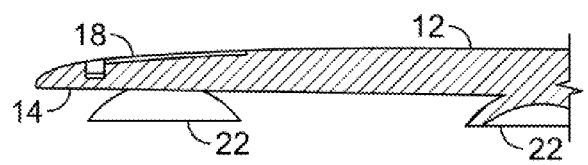
FIG. 3 is detailed, fragmentary, cross-sectional view of the left portion of the floormat of FIG. 2.
Figure 4:
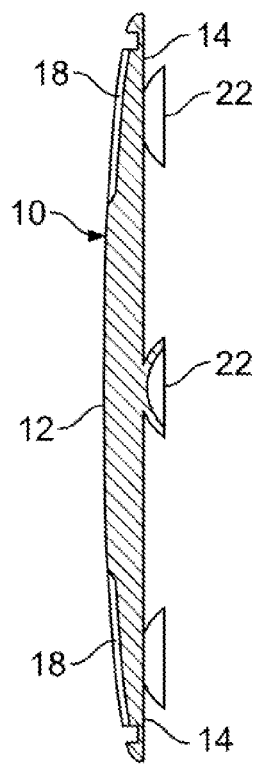
FIG. 4 is a cross-sectional view taken a long line 4-4 FIG. 1.
Figure 5:
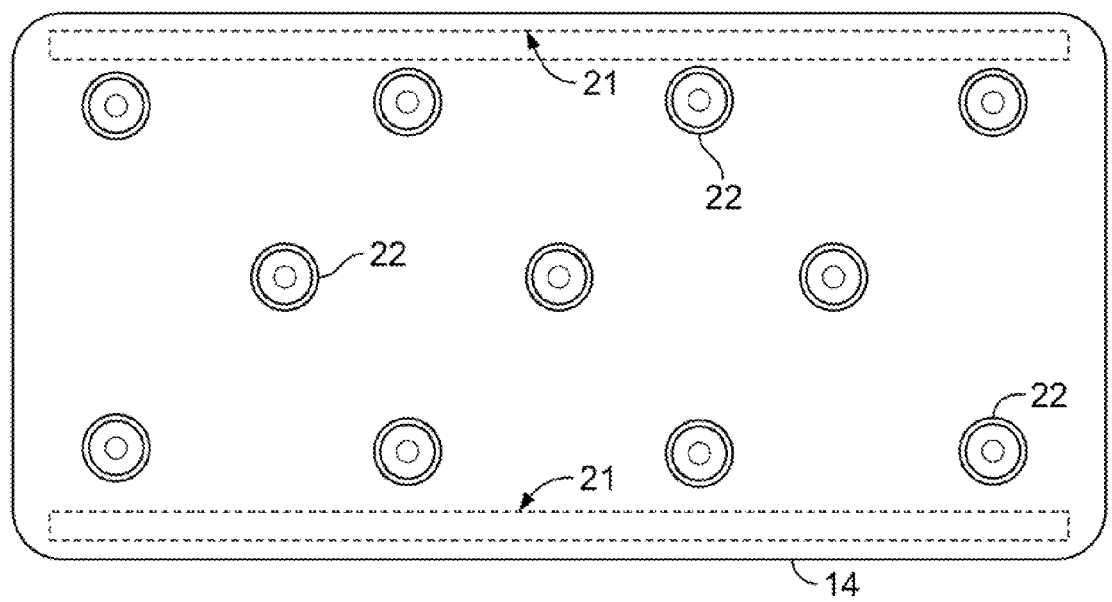
FIG. 5 is a bottom view of the mat of FIG. 1.
Figure 6:
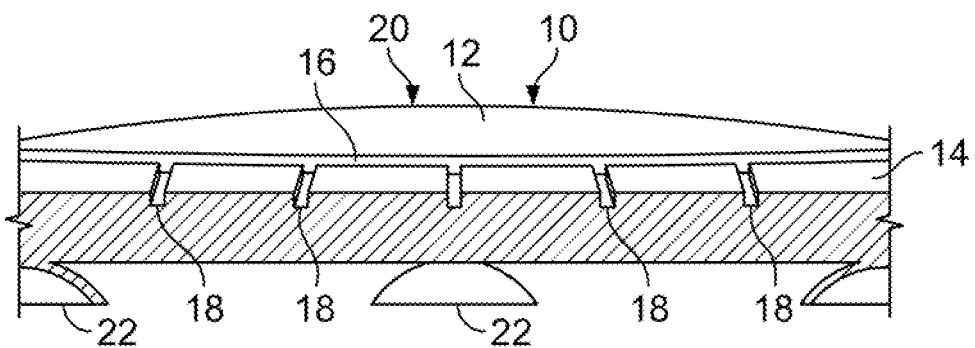
FIG. 6 is a fragmentary, cross-sectional view taken a long line 6-6 FIG. 1.
Figure 7:
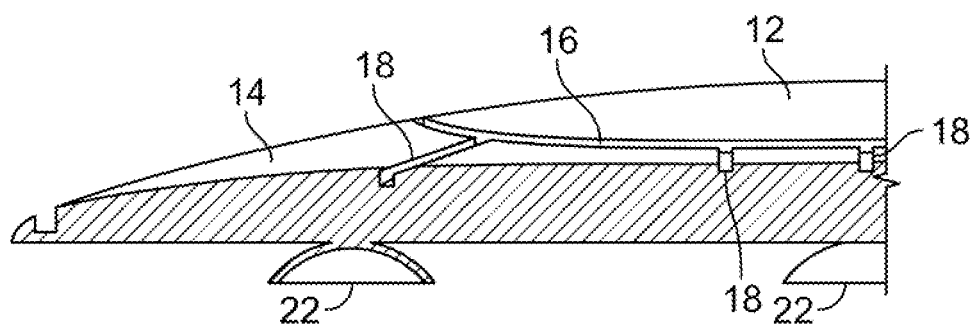
FIG. 7 is a fragmentary, cross-sectional view taken a long line 7-7 FIG. 1.

Referring to FIGS. 1-7, the illustrated floormat 10 may be made of an elastomeric material such as PVC, or a rubber, either synthetic or natural. Other materials such as polyurethane foam, a "memory" foam as well as materials commonly used in anti-fatigue mats are contemplated also. It is also desirable to make the mat material nonflammable, and to avoid allergic reactions, latex-free. In addition, the mat material contains static-dissipative properties ($10^9$ ohms per sq. ft.) and an anti microbial agent. Further, the mat material may be non-staining, UV resistant and resistant to most chemicals. The disclosed embodiment, designed specifically for anti-fatigue use and surface drainage, is made with chemically expanded closed-cell foam, manufactured with 100% virgin raw material having the specifications outlined in Table 1. It is appreciated that the specifications may vary for other embodiments.

TABLE 1

| GAUGE: | 650 mils (⅝ inch) | Tolerance +/− 12 mils (+/− 0.012 inch) |
|---|---|---|
| WEIGHT/AREA: | 128 oz/yd$^2$ | Tolerance (+/− 5 oz./yd$^2$ minimum) |
| DENSITY: | 17 lb/ft$^3$ | Tolerance ± 1 lb/ft$^3$ |
| HARDNESS: | 40-50 | Durometer Hardness ASTM D-2240-86 |
| TENSILE STRENGTH: | 125 lb/in$^2$ minimum | Tensile Strength, Die 'C' ASTM D-638-90 |
| ELONGATION @ 100%: | 130% | Elongation ASTM D-638-90 |
| TEAR STRENGTH: | 30 lb/in$^2$ minimum | Tear Strength ASTM D-1004-90 |
| FLAME RESISTANCE: | Pass | Federal Motor Vehicle Safety Standard 302 Flame Resistance |
| FLAME RESISTANCE: | Pass | Methenamide Pill Test DOC FF 1-70 |
| LIMITED OXYGEN INDEX: | >24% | ASTM D-2863-77 |
| OPERATING TEMPERATURE RANGE: | 30° F.-110° F. | Manufactured by an ISO 9001:2000 certified company |

It is highly desirable to provide a mat 10 that is disposable and intended for a single use. Accordingly, the mat material need not be highly durable and wear-resistant. For such disposable models, wear resistant coatings are not contemplated. To keep mat 10 sanitary, it can be cleaned, disinfected or sterilized, as appropriate. Thereafter mat 10 can be rolled up or packaged flat in a plastic material before shipment.

Mat 10 as shown is 36 inches long (0.9 m) and 17 inches (0.4 m) wide, although other overall dimensions are contemplated for other embodiments. Mat 10 has a central section 12 encircled by an annular, tapered apron 14. Apron 14 is about 3.5 inches (8.9 cm) and has a slope that ranges between about 4 degrees to 30 degrees.

Central section 12 is crowned, that is, it slopes downwardly in every direction away from its apex 20, which is located at the center of the mat 10. In one embodiment the radius of curvature along the longitudinal centerline of the central section 12 is about 260 inches (6.6 m). In that embodiment the radius of curvature along a transverse centerline is about 58 inches (1.5 m). The advantages of crowning as described hereinafter will occur when the radius of curvature in central region 12 is less than a maximum of 500 inches (1.3 m). In one embodiment central section 12 has a thickness or height of 0.75 inch (1.9 cm) at its apex 20. It is desirable to have the height or thickness at apex 20 in the range of 0.5 to 1.5 inches (1.3 to 3.8 cm). With a thickness at apex 20 of about 0.75 inch (1.9 cm), the height or thickness of the central section 12 at its perimeter may be about 0.35 inch (9 mm), but for various other embodiments it will be desirable to keep the thickness at the perimeter in a range of 0.2 to 0.6 inch (5 to 15 mm).

The margin between central section 12 and apron 14 is marked by an optional, annular groove 16. The groove 16 runs parallel to the short sides and about 4 degrees to the long sides of mat 10 except at its rounded corners. Projecting outwardly and transversely from groove 16 across apron 14 are a number of channels 18. The width and depth of channels 18 are similar to that of groove 16, although they can be sized differently in other embodiments. In one embodiment channels 18 were 0.25 inch (6 mm) wide and 0.06 inch (1.5 mm) deep, although this dimension can vary in alternative embodiments. It is advantageous to have these channels 18 in a range of ⅛ through ½ inch (3 through 13 mm) wide and 0.03 to 0.25 inch (0.7 to 6 mm) deep. In most embodiments, central section 12 and apron 14 will be integral components that are molded at the same time to form a common core. A series of gutters 34, 36, 38, and 40, in apron 14 around central section 12 communicate with the distal end of channels 18 and may be fitted with an optional drain assembly, having a structure that will be described presently. Outlet gutter 42 communicates with the junction of gutters 40 and 36 and allows drainage off floormat 24. In some embodiments the outlet gutter can be positioned differently and more than one outlet gutter may be employed.

A number of integral, molded suction cups 22 project from the underside of mat 10. In this embodiment suction cups 22 are molded simultaneously with the main body of the mat, that is, with central section 12 and apron 14. Suction cups 22 may be 0.5 to 1.5 inches (1.3 to 3.8 cm) in diameter, although other sizes are possible. In this embodiment three equidistant suction cups 22 are placed along the centerline on the underside of central section 12. On either side of this centerline two sets of four equidistant suction cups 22 are placed in lines parallel to the centerline to form a staggered, diamond pattern of suction cups. In other embodiments a different number of suction cups may be laid in a different pattern.

In some embodiments, suction cups will not be employed but the underside of the mat will have a nonslip surface. As shown in phantom in FIG. 5, a double sided adhesive tape 21 may be attached to the underside of the mat to keep it in place. The adhesive on the side of the tape attached to the mat would be a permanent adhesive, while the adhesive on the exposed surface would be repositionable. Tapes of this type are available from 3M. A paper liner could be employed to cover the adhesive during shipment and storage. Alternatively, the entire underside of the mat may be finished with a tacky substance or an adhesive. In other embodiments, the mat material itself may be inherently nonslip. In still other embodiments the underside may be roughened or may have a large number of nubs that grip the floor. Alternatively, the underside may have a plurality of domed depressions that create suction when pressed onto the floor. Moreover, the top side of the mat 10 (section 12 and apron 14) can have a nonslip finish as well, which can be accomplished by providing a roughened surface. Alternatively, the mat material may contain a chemical agent, giving all surfaces of the mat a nonslip finish.

Various embellishments and decorations are contemplated for mat 10. In keeping with customary colors for operating rooms, mat 10 can be colored blue either by incorporating a die or by applying a colored coating to the mat. In some embodiments, central section 12 and apron 14 may be colored differently. Also, advertising logos may be placed at various positions on mat 10. For example, a drug brand may be advertised in large letters on the central section 12.

Figure 8:
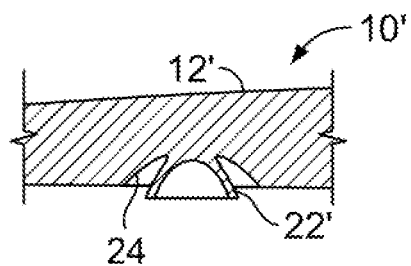
FIG. 8 is a detailed, fragmentary, cross-sectional view of a portion of a floormat with a recessed suction cup that is an alternate to that of FIG. 2.

Referring to FIG. 8, a modified mat 10' is arranged in a manner similar to that shown in FIG. 1. In this Figure, components corresponding to those previously illustrated in FIG. 1 will have the same reference numerals but marked with a prime ('). In particular, suction cup 22' has a shape similar to that previously illustrated but is located in a recess 24 on the underside of mat 10'. Suction cups 22' can be arranged in a pattern similar to that shown for the mat 10 of FIG. 1.

Referring to FIGS. 9-11, another floormat 24 is illustrated, again having rounded corners. Floormat 24 may be made of material similar to that described above in connection with the other embodiments and will have the previously mentioned adhesive tape (tape 21 of FIG. 5). In this embodiment the topside 26 is relatively flat except for a number of longitudinal channels 28. While twenty such channels are illustrated, other embodiments can have a greater or lesser number. Ridges 26A of topside 26 are located between channels 28. Gutters 134, 136, 138, and 140 encompass regions 26A and communicate with the distal ends of channels 28 (regions 26A being referred to as a central region having channels 28).

Outer border regions 26B, 26C and 26D are located to the outside of the gutters 134, 136, 138, and 140, which gutters are arranged similarly to the gutters of FIG. 1. Outlet gutter 142 is aligned with gutter 140 at its intersection with gutter 136. Outlet gutter 143 is aligned with gutter 140 at its intersection with gutter 134. In some embodiments one of the discrete outlet gutters 142 or 143 may be eliminated.

The floors of each of the channels 28 have a central peak 30 equidistant from the channel ends for dividing any fluids that enter the channels. The channels 28 are illustrated with a rectangular cross-section, although in other embodiments the cross-section may be semicircular, oval, polygonal, etc. Additionally, the width of the channels may vary along their lengths, in some embodiments.

The peaks of border regions 26B, 26C and 26D are all at substantially the same elevation as central region 26A. These outer regions 26B, 26C and 26D are beveled, sloping outwardly from their peaks to form the outer edge of the mat 24. Outer region 26B is approximately 2 inches (51 mm) wide, while outer region 26D is around ½ inch (13 mm) wide. Outer regions 26C are each 1½ inches (38 mm) wide. All these dimensions may vary in other embodiments.

Channels 28 have a depth that increases for directions away from central peaks 30. Moreover, the elevation of the floors of channels 28 decline for directions away from central peaks 30. Accordingly, fluid entering channels 28 flows away from the central peak 30 to the channel ends and into the into the gutters 134 and 136, and, if present, the drainage pipes shown in FIG. 12.

In one embodiment floormat 24 has an overall length of 35 inches (0.9 m) and an overall width of 22 inches (0.56 m). In this embodiment the overall thickness of floormat 24 (measured at ridges 26A of topside 26) was ⅝ inch (16 mm). The channels 28 are 0.2 inch (5.1 mm) wide and are distributed with a channel to channel spacing (measured from the center of one channel to the center of another) of 0.7 inch (18 mm). The depth of the channels 28 varied linearly from a minimum of ⅛ inch (3.2 mm) at central peaks 30 to a maximum of ⅜ inch (9.5 mm) at the outlet ends. It will be appreciated that these dimensions and proportions can be varied for other embodiments.

The foregoing mat 24 may be made with nonslip surfaces in the manner described above for the other embodiments. Preferably, the underside 32 of the mat 24 will employ the double sided adhesive tape as shown in phantom in FIG. 5 and described for the other embodiments. Also, in some embodiments the entire underside 32 of the mat 24 may be finished with a tacky adhesive as described for the other embodiments, in order to keep the mat in place. Alternatively, the underside 32 of the foregoing mat 24 can have suction cups similar to those described above.

Figure 12:
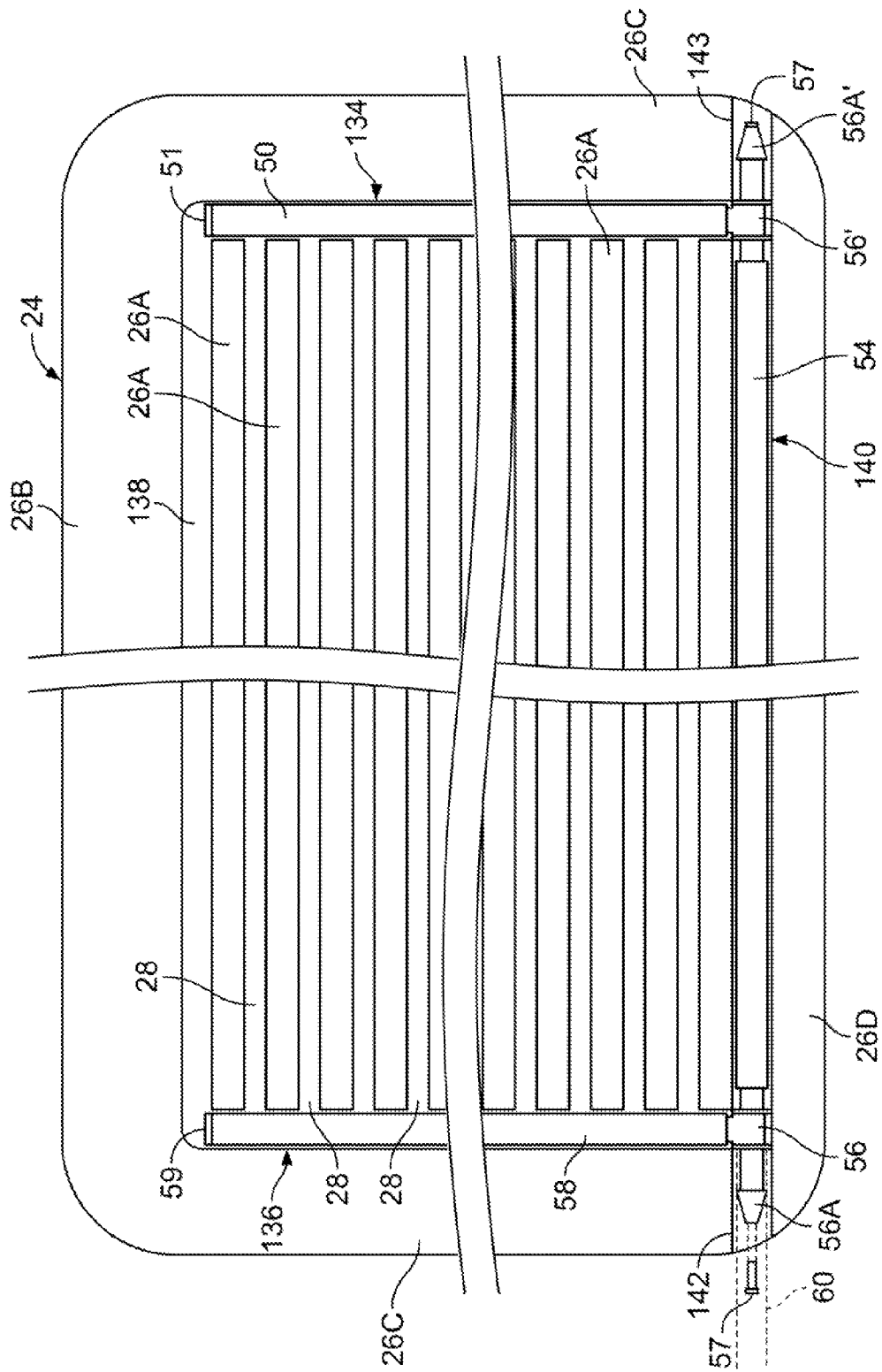
FIG. 12 is a detailed plan view of the floormat of FIG. 9 with portions broken away and with various tubes installed.

Gutters 134, 136, 140, 142 and 143 are each ½ inch in width to allow room to house the optional drainage assembly illustrated in FIG. 12. In most embodiments, gutter 138 will remain empty and will not be used to house any tubing or drainage pipes. Thus gutter 138 may be narrower than the other gutters, having a width of 0.3 inch (7.6 mm).

Figure 13:
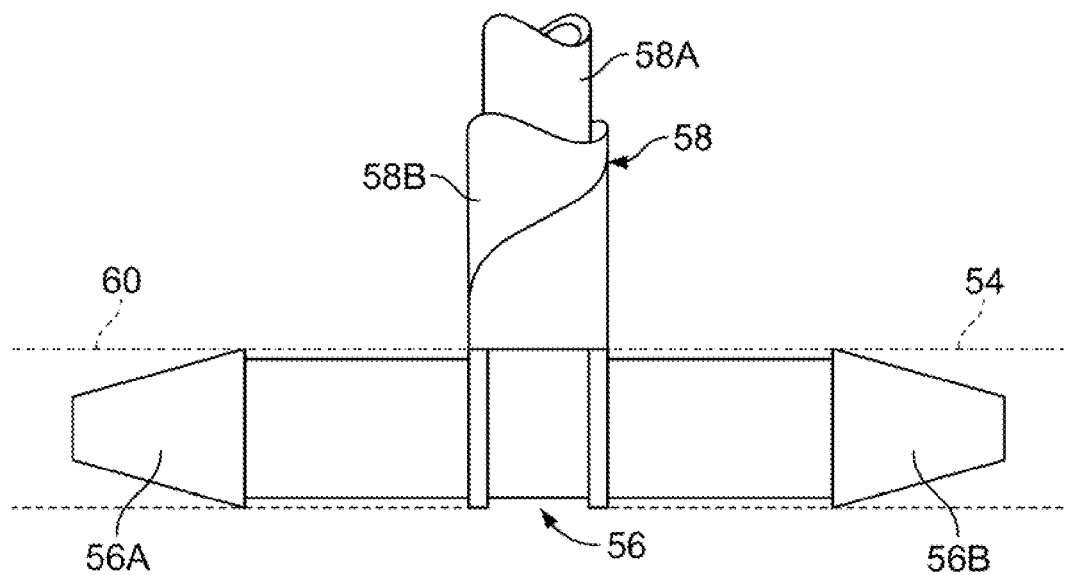
FIG. 13 is a plan view of a T-fitting in FIG. 12.
Figure 14:
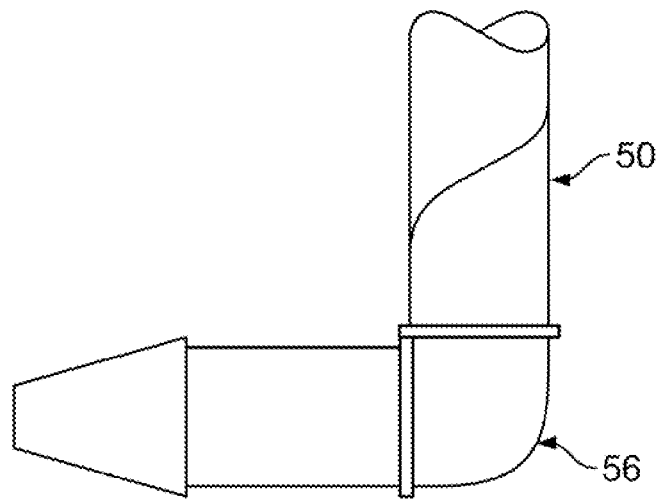
FIG. 14 is a plan view of an elbow that may be used in the floormat of FIG. 12.
Figure 15:
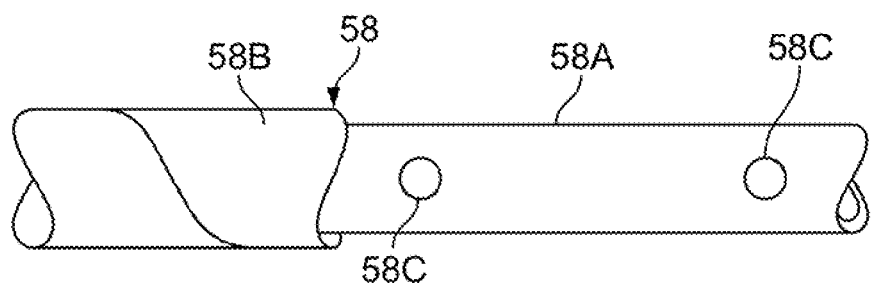
FIG. 15 is a side view of a fragment of a tube in FIG. 12.

Referring to FIGS. 12-15, FIG. 12 shows the mat of FIG. 9 fitted with a drain assembly, which is shown in further detail in FIGS. 13-15. In particular, drainage pipes 50 and 58 will be placed in gutters 134 and 136, respectively. Pipes 50 and 58 may have identical structure and may be include tubing made of PVC or other materials.

Plug 59 is 0.47 inch in length (1.2 cm) and will be inserted in the distal end of pipe 50. The other end of pipe 58 will be fitted with one branch of T fitting 56, whose two other aligned branches lie in gutters 140 and 142. The branch of fitting 56 lying in gutter 142 (gutter 142 also referred to as an outlet) is shown as a conduit terminating in a conically flared head 56A designed to lock into tubing 60. When shipped, head 56A is sealed with removable plug 57, shown removed to accommodate tubing 60.

FIG. 13 shows the opposite branch, also in the form of a conduit terminating in a conically flared head 56B. The third branch of T fitting 56 is the same as the other two branches and its conical head is inserted into pipe 58. In this embodiment the outside diameter of the conical heads (e.g. head 56A) is ⁵⁄₁₆ inch (8 mm), although other dimensions may be employed in other embodiments.

Plug 51 will be inserted in one end of pipe 50. The other end of pipe 50 will be fitted with one branch of T fitting 56', which is identical to fitting 56 on pipe 58. The two other aligned branches of fitting 56' lie in gutters 140 and 143. The branch of fitting 56 lying in gutter 143 (gutter 143 also referred to as an outlet) is shown as a conduit terminating in a conically flared head 56A' designed to lock into tubing, but in this case sealed with plug 57. Thus, a user can conveniently choose to connect tubing 60 to either head 56A or 56A'.

In some cases, fitting 56' (or fitting 56) may be replaced with elbow 52, shown in FIG. 14. In this case the proximal end of pipe 50 in gutter 134 will communicate through elbow 52 to pipe 54 in gutter 140, without communicating to gutter 143. Pipe 54 may be a simple plastic tube without the apertures or sleeves associated with pipes 50 and 58.

Referring to FIG. 15, drainage pipe 58 comprises plastic tubing 58A covered with a porous sleeve 58B. Tubing 58A may be made of a flexible plastic such as polyurethane or polyvinyl chloride with an outside diameter of 0.4 inch (1 cm), although other materials and dimensions may be employed in other embodiments. Sleeve 58B may be a polyester knit formed from a strip that is spirally wound and stitched to form a tube. Alternatively, a fabric strip can be curled back and stitched to form a straight, longitudinal seam. In other embodiments sleeve 58B may be knit or woven directly into a tubular form. In all embodiments, sleeve 58B will serve as a noise reducer and debris filter. In some embodiments, sleeve may be a chamois-like material such as a nonwoven viscose fabric.

Figure 16:
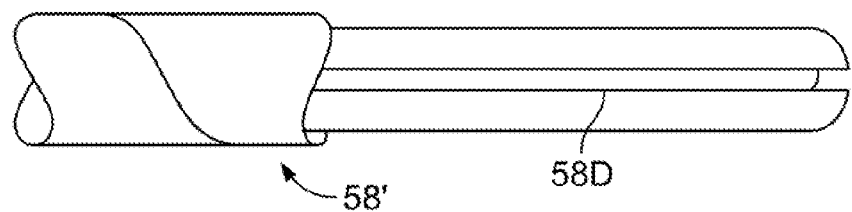
FIG. 16 is a side view of a tube that is an alternate to that of FIG. 15.

Tubing 58A has a series of longitudinally aligned apertures 58C positioned to coincide with the outer end of channels 28, that is, one aperture for each of the channels 28. The diameter of apertures 58C may vary, though the preferred diameter is ¹⁄₁₆ inch (1.59 mm). In other embodiments these apertures may be replaced with the longitudinal slit 58D shown in FIG. 16, which is a feature of a pipe 58' that is otherwise identical to that shown in FIG. 15. Sleeve 58B prevents debris from passing through either apertures 58C (FIG. 15) or slit 58D (FIG. 16). Also, sleeve 58B acts as a dampener to provide some noise suppression.

Figure 17:
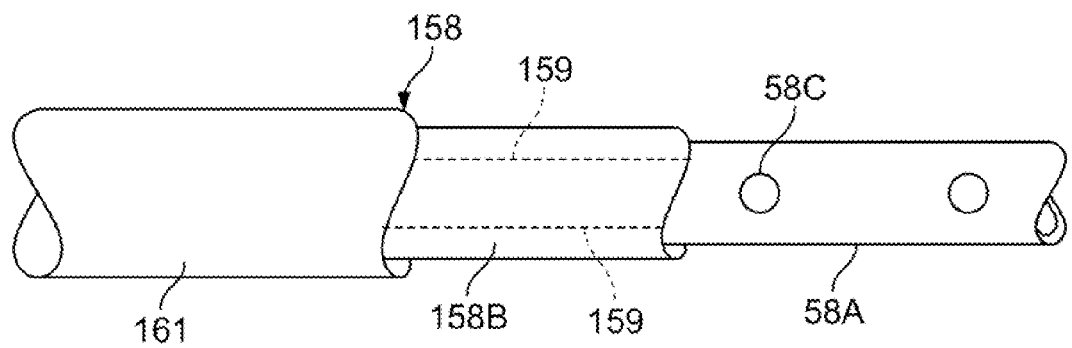
FIG. 17 is a side view of a tube that is an alternate to that of FIGS. 15 and 16.

Referring to FIG. 17, an alternate drainage pipe 158 has the same tubing as shown in FIG. 15 (tubing 58A). However, the spiral wrapped sleeve 58B is replaced with a strip 158B made of the same material. Strip 158B is laid longitudinally over apertures 58C and partially wrapped around the tubing 58A (for example 270°), leaving a gap between edges 159. In this embodiment strip 158B is a synthetic chamois-like material (e.g., nonwoven viscose fabric) designed to filter particles that might enter into aperture 58C, as well as providing mechanical dampening and noise suppression. Strip 158B is covered and held in place by graded sleeve 16, which also offers some coarse filtering. In one embodiment sleeve 161 was braided from PET yarns (e.g., a Flexo PET sleeve from Flextech Inc. of Sparta, N.J.).

Figure 18:
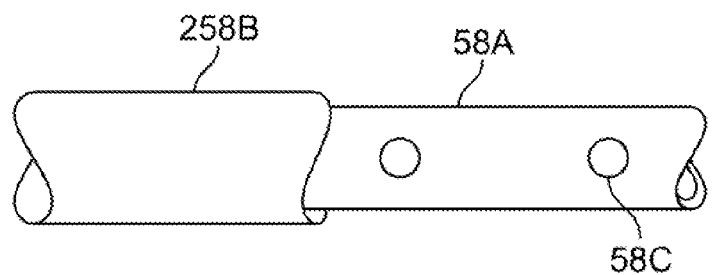
FIG. 18 is a side view of a tube that is an alternate to that of FIGS. 15-17.

Referring to FIG. 18, previously mentioned tubing 58A is covered with a sleeve 258B made of synthetic chamois-like material (e.g., nonwoven viscose fabric) either formed originally as a tube, or formed into a tube by joining two edges of an elongated strip. Again, sleeve 258B provides filtering and noise suppression.

Referring again to FIG. 12, flexible tubing 54 is shown lying in gutter 140 and connecting between the right branch of fitting 56 and the left branch of fitting 52. The left branch of fitting 56 will lie in gutter 142 and connect to a suction tube 60 (shown in phantom). Tubing 54 will lack the apertures and sleeve of pipes 50 and 58 and may be held in place by an adhesive such as cyanoacrylate or the like.

Pipes 50 and 58 may also be glued in place but only with a narrow bead of glue so that the sleeves (e.g., sleeve 58B) remain permeable and the apertures (e.g. apertures 58C) remain open. In this embodiment apertures 58C (or 58D) will point at a depressed angle of elevation of about 45° below horizontal (between a 4 and 5 o'clock position). It will be appreciated that pipe 50 will be made and installed in a similar manner.

It will be further appreciated that although an outlet is shown in one corner of the mat as gutter 142, the outlet can be placed anywhere along the gutters of the mat. Further, multiple outlets may be created to allow the flexibility of alternate outlets or to permit connection of additional suction tubes 60. Some embodiments may have multiple outlets that have removable plugs or dams so the user can choose where to connect one or more suction tubes 60. On the other hand, some embodiments will have only one outlet gutter.

The foregoing drainage pipes may be fitted in the gutters of the embodiment of FIGS. 1-7. The gutter system of FIGS. 1-7 has a similar configuration as described above with one significant exception: fitted in gutter 38 is a drainage pipe with apertures and sleeving as shown in FIG. 15 or 16. Accordingly, the width of gutter 38 will be equal to the width of the other gutters. Consequently, previously mentioned caps 51 and 59 are replaced with elbows (not shown) that connect to this drainage pipe within gutter 38. In addition, previously mentioned tubing 54 is replaced by a fourth drainage pipe, similar to that of FIG. 15 or 16. For the pipes of FIG. 15, the apertures 58C are spaced to align with the outer end of channels 18. Also, because gutter 42 is the only discrete outlet gutter the elbow of FIG. 14 will be installed at the junction between gutters 34 and 14.

To facilitate an understanding of the principles associated with the foregoing apparatus, the operation of the embodiment of FIG. 12 will be briefly described. The above described mat 24 may be removed from its plastic packaging (not shown). The paper liners (not shown) are removed from the underside of the mat, exposing the repositionable adhesive tape (tape similar to tape 21 of FIG. 5). The mat 24 can then be positioned and laid on the floor at the location where a user or other personnel are expected to stand. Stepping on mat 24 will cause the adhesive tape 21 to grip the floor and hold the mat 10 in place.

Mat 10 is made of resilient material that will increase comfort, reduce fatigue and, in general, ease the burden of standing during a long procedure. Also, channels 28 are relatively small and do not substantially degrade the cushioning, anti-fatigue effect. Also, these channels 28 are sufficiently small to avoid any risk of tripping.

During the procedure fluids may fall onto mat 24. Fluids tend to fall into channels 28 and flow away from peak 30 (FIG. 9) toward gutters and 134, and 136. Suction applied by hose 60 through head 56A will create a vacuum in pipes 50, 54 and 58. Accordingly, fluid flowing to the ends of channels 28 will be sucked into the apertures 58C of pipes 50 and 58. Since the apertures 58C point slightly downwardly they will efficiently aspirate the draining fluid. Debris or other particles in the fluid will be filtered by sleeve 58B (embodiment of FIG. 15) or by sleeves 158B and 161 (embodiment of FIG. 17), or by sleeve 258B (embodiment of FIG. 18). Also, the foregoing sleeves can suppress noise caused by vibration in tubing 58A.

The suction applied by hose 60 through head 56A will create a vacuum in pipes 50, 54 and 58. Accordingly, fluid flowing to the ends of channels 28 will be sucked into the apertures 58C of pipes 50 and 58. Debris or other particles in the fluid will be filtered by sleeve 58B (embodiment of FIG. 15) or by sleeves 158B and 161 (embodiment of FIG. 17), or by sleeve 258B (embodiment of FIG. 18). Also, the foregoing sleeves can suppress noise caused by vibration in tubing 58A.

Fluid in pipe 50 will flow through fitting 56', pipe 54 and fitting 56, before being evacuated through hose 60. Fluid in pipe 58 will flow through fitting 56 and be evacuated through hose 60, as well. Hose 60 may be connected to a suction system such as may be found in a hospital operating room.

Consequently, the user will have a dry place to stand with less chance of contaminated, corrosive or infected fluids seeping through any foot covering worn by the user. Also, a dry surface will reduce the chance of slipping and falling.

If the user is expected to work in several locations, multiple mats can be placed at those sites. Of course, mats can be provided for other assistants in the vicinity.

If pipes are not used in the drainage system, the fluids will be naturally drain through gutters 134, 136, 140 before exiting through outlet gutters 142 in 143 (unless one of the outlet gutters is blocked by a dam or other means). Fluids draining off mat 24 can be removed by mopping, absorbent towels, or by using an external vacuum device.

After the procedure is completed, personnel can remove the mat 24, place it into a leakproof disposal bag and discard the mat. Often, the mat will require special handling since it may contain material considered corrosive or biological waste representing a danger of infection or contamination.

The operations of the floormat 10 of FIGS. 1-7 will be briefly described. The above described mat 10 is laid on the floor next to a location where a user or other personnel are expected to stand. Stepping on mat 10 will cause the suction cups 22 to grip the floor and hold the mat 10 in place.

Mat 10 is made of resilient, material that will increase comfort, reduce fatigue and, in general, ease the burden of standing during a long procedure. In addition, while the apron 14 is thinner, it is still sufficiently thick to provide a comforting, anti-fatigue effect. Also, channels 18 (as well as groove 16) are relatively small and do not substantially degrade the cushioning, anti-fatigue effect on apron 14. Also, these channels 16 and 18 are sufficiently small to avoid any risk of tripping.

During the procedure fluids may fall onto mat 10. Fluids falling on central section 12 will tend to shed from the surface and drain through channels 16 and 18. Fluids eventually flow into gutters 36, 38, and 40 before exiting through outlet gutter 42. Fluids falling on apron 14 will shed fluids directly or through channels 18.

Fluids shed from mat 10 will drain onto the floor but at locations where the user is normally not standing. During a procedure, any fluids that drain off the mat 10 can be cleaned up with either a suction device or by throwing towels on the fluids, although in many instances these fluids will remain on the floor until completion of the procedure.

The foregoing mats may be used in an operating room where a surgeon must often deal with fluids spilling in the vicinity where the surgeon is standing. Many surgical procedures involve the discharge of bodily fluids or the washing or irrigation of various sites, all tending to result in spills, either intended or unintended. The foregoing drainage tends to keep the surgeon's feet dry and reduce the danger of slipping and falling. Also spills occurring in an operating room may represent a biohazard and care must be taken to avoid seepage through footwear making contact with the skin. While removing fluid from the vicinity is an important consideration, preventing user fatigue is also important. The resilient surface presented by the foregoing floormat will reduce user fatigue, while simultaneously dealing with spilled fluids.

Various other environments exist where a person may be standing during a procedure and where fluid may be spilled in the vicinity of where the person stands. For example, boaters may stand on a deck that is periodically sprayed or splashed by seawater. In some cases the boater may need to operate, repair or clean equipment and seawater may drain from the equipment during the procedure.

Also fishermen and hunters may need to clean, dress and prepare their catch or kill. In such cases fluids may run onto the ground due to the release of body fluids or water used to clean the work site. Butchers will experience a similar situation when cutting and dressing meat at a butcher shop.

In addition, many technicians and hobbyists in the automotive field, gun repair/maintenance field, or other mechanical repair fields may spill fluids used to clean parts or may spill fluids used by the machinery (hydraulic fluid, coolant, brake fluid, transmission fluid, refrigerant, etc.)

Ordinary consumers may also deal with spills in the vicinity of where the person stands. Fluids are often encountered when preparing foods or using the sink in a kitchen. In addition, various cleaning or repair tasks conducted throughout the house or the yard may involve fluid spills as well.

In all these instances one wishes to avoid standing in spilled fluids. In some cases avoiding the discomfort of wet feet is an important consideration, but in other instances the fluids involved can be hazardous or deleterious. For example, some fluids can be slippery and increase the danger of falling. Other fluids may be corrosive and can damage either footwear or the foot itself.

It is appreciated that various modifications may be implemented with respect to the above described, preferred embodiments. While the illustrated grooves and channels are shown having a rectangular cross-section, in some embodiments their cross-section may be rounded, triangular, polygonal, oval, or shaped otherwise. Also in some embodiments the channels may be so close together that a cross-section through the mat reveals a sinuous or sawtooth pattern. Moreover, in some embodiments the path of the channels may be curved. In some cases, the paths of the channels may be in the form of nested arches or may be arranged in a herringbone pattern. In addition, the mats in some embodiments may have perforations that allow the fluids to pass directly through the mat. Furthermore, in embodiments like that of FIG. 1, not all of the channels will reach the border of the central section, and some channels may run across just the apron. Moreover, instead of a central section surrounded on all sides by an apron, in some embodiments the central section may be a center strip running across the full length of the mat and bordered on either side by a separate pair of tapered aprons.

Obviously, many modifications and variations of the present invention are possible in light of the above teachings. It is therefore to be understood that within the scope of the appended claims, the invention may be practiced otherwise than as specifically described.

The invention claimed is:

1. A floormat arranged to handle fluids:
    (a) said floormat having a topside and an underside and being formed, at least in part, of compressible and resilient material; and
    (b) said topside having a spaced plurality of channels feeding at least one gutter on a side of the gutter that has a height at least as great as the opposite side thereof, said channels being sized to avoid a risk of tripping, said topside having a central region and a border region, said border region tapering outwardly from said at least one gutter, said central region occupying most of said topside and being substantially flat throughout except for the channels, said border region having a height no greater than that of said at least one gutter, said floormat comprising:
    tubing lying in said at least one gutter and occupying at least most of its length, said tubing having one or more intake apertures located downstream of at least some of said plurality of channels.

2. A floormat according to claim 1 comprising:
    at least one outlet formed in said border region and adapted to drain fluids in said at least one gutter off said floormat.

3. A floormat according to claim 2 adapted to cooperate with a source of suction, said floormat comprising:
    a fitting mounted at said one outlet and adapted to attach to said source of suction.

4. A floormat according to claim 1 wherein each of the channels have in the central region a floor sloping in opposite directions from a central peak, said channels for most of their lengths become deeper for positions further from the central peak.

5. A floormat according to claim 1 comprising:
    at least one outlet formed in said border region and adapted to drain fluids from said at least one gutter, said at least one gutter bordering and communicating with said spaced plurality of channels.

6. A floormat according to claim 5 wherein said at least one outlet comprises a spaced pair of outlets.

7. A floormat according to claim 6 wherein drainage off said floormat is provided through one of said pair of outlets, the other one of said outlets being restricted from conducting fluid drainage.

8. A floormat according to claim 6 wherein drainage off said floormat is provided through both of said pair of outlets, neither one of said outlets being prevented from conducting fluid drainage.

9. A floormat according to claim 1 wherein said at least one gutter borders said spaced plurality of channels and communicates with them, said floormat comprising:
    at least one outlet formed in said border region and adapted to drain fluids from said at least one gutter.

10. A floormat according to claim 9 wherein said at least one outlet is adapted to drain fluids in said at least one gutter off said floormat.

11. A floormat according to claim 9 comprising:
a suction tube connecting to said tubing and extending off said central region and said border region.

12. A floormat according to claim 9 wherein said tubing has a plurality of intake apertures located downstream of at least some of said plurality of channels.

13. A floormat according to claim 12 wherein each of said plurality of intake apertures are in alignment with a different corresponding one of said plurality of channels.

14. A floormat according to claim 13 wherein said at least one outlet comprises:
a pair of outlets formed in said border region and connected to said at least one gutter, said tubing having a first and a second fitting, each located at a different corresponding one of said pair of outlets, said first fitting having a branch for draining fluid into an adjacent one of said pair of outlet.

15. A floormat according to claim 14 wherein said spaced plurality of channels are parallel and have floors sloping in opposite directions from a central peak, said at least one gutter including a first gutter and a connecting pair of gutters extending perpendicularly from opposite ends of said first gutter, said connecting pair of gutters being perpendicular to said spaced plurality of channels, said pair of outlets connecting to opposite ends of said first gutter.

16. A floormat according to claim 9 comprising:
a porous sleeve encompassing said tubing for filtering fluid destined for said one or more intake apertures.

17. A floormat according to claim 16 comprising:
a braided sleeve encompassing said porous sleeve for filtering more coarsely than said porous sleeve, fluid destined for said one or more intake apertures.

18. A device according to claim 16 wherein said porous sleeve has a composition chosen for reducing noise produced at said tubing.

19. A floormat according to claim 1 wherein said border region is tapered outwardly from, and is at least as wide as, said at least one gutter.

20. A floor mat according to claim 1 wherein said channels have a width of at most 0.5 inch.

21. A floor mat according to claim 1 wherein said channels have a depth of at most 0.25 inch.

* * * * *